United States Patent [19]

Sugimori et al.

[11] Patent Number: 4,555,561
[45] Date of Patent: Nov. 26, 1985

[54] POLYURETHANE RESIN COMPOSITION

[75] Inventors: Masaru Sugimori; Koichiro Sanji, both of Takatsuki, Japan

[73] Assignee: Sun Star Giken Kabushiki Kaisha, Takatsuki, Japan

[21] Appl. No.: 643,700

[22] Filed: Aug. 24, 1984

[30] Foreign Application Priority Data

Sep. 7, 1983 [JP] Japan ................. 58-165424

[51] Int. Cl.$^4$ ............ C08G 77/26; C08G 18/66; C08K 9/06
[52] U.S. Cl. .................. 528/26; 524/869; 528/28
[58] Field of Search ............ 524/869; 528/28, 26

[56] References Cited

U.S. PATENT DOCUMENTS

| | | | |
|---|---|---|---|
| 3,627,722 | 12/1971 | Seiter | 524/869 |
| 3,711,445 | 1/1973 | Chu | 524/869 |
| 3,746,738 | 7/1973 | Pepe | 528/28 |
| 3,856,756 | 12/1974 | Wagner | 528/28 |
| 3,886,226 | 5/1975 | Asai | 528/28 |
| 4,067,844 | 1/1978 | Barron | 528/28 |
| 4,345,053 | 8/1982 | Rizk | 528/28 |
| 4,374,237 | 2/1983 | Berger | 528/28 |

FOREIGN PATENT DOCUMENTS 51-60298  5/1976  Japan ................. 528/28
53-35798  4/1978  Japan ................. 528/28

Primary Examiner—C. Warren Ivy
Attorney, Agent, or Firm—Wegner & Bretschneider

[57] ABSTRACT

A polyurethane resin composition, which comprises (A) a urethane prepolymer composition containing 0.5 to 15.0% by weight of an active isocyanate group which is prepared by reacting a polyoxyalkylene ether polyol and/or polyester polyol and an excess amount of a polyisocaylante compound, and (B) as an adhesion-promoting agent 0.05 to 5.0% by weight of a reaction product of an amine compound containing at least one alkoxysilyl group of the formula:

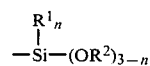

wherein $R^1$ and $R^2$ are the same or different and are each a alkyl having 1 to 4 carbon atoms, and n is 0, 1 or 2, and an excess amount of a carbonyl compound. Said polyurethane resin composition has excellent adhesion properties and can show also excellent adhesiveness to metals which are hardly adhered with the conventional compositions and is useful as an adhesive, sealant and coating agent in various technical fields.

4 Claims, No Drawings

POLYURETHANE RESIN COMPOSITION

The present invention relates to a novel polyurethane resin composition useful as an adhesive and sealant and in any other utilities. More particularly, it relates to a polyurethane resin composition having excellent adhesion properties to various substances to be adhered, which comprises an active isocyanate group-containing urethane prepolymer composition and a reaction product of a specific alkoxysilyl group-containing amine compound and a carbonyl compound.

Polyurethane resins are usually easy in the control of the molecular weight and hence there can easily be obtained various grades of products having a wide range of physicochemical properties, for example, from a tacky liquid to a rubbery elastomer and further a tough plastic material. Accordingly, the polyurethane resins are very important as a material for various plastic formed products, plastic foam products and rubber processing products in the fields of civil engineering, buildings, automobile parts, electrical products, and further as a material for paints, adhesives and sealants.

In order to use polyurethane resins as a material for adhesives, sealants, paints or coating agents, the composition should have excellent adhesiveness to the substances to be adhered or coated. The known polyurethane compositions are, however, somewhat inferior in the adhesion properties to inorganic substances such as metals, glasses and concretes and organic substances such as plastics, rubbers and various substances to be coated, and hence, it is usually applied to the substances to be adhered or coated after pre-treatment with a adhesion-promoting primer, that is, after applying an organic solvent solution of a polyisocyanate compound, silane coupling agent, or titanate coupling agent to the surface of the substances to be adhered or coated. Thus, such a method has drawbacks of increased labor for the adhesion work and coating work and also increase of production cost.

It has been proposed to improve the adhesion properties of the polyurethane resin composition by incorporating a larger amount of an active isocyanate group into the prepolymer or incorporating an adhesion-promoting agent (e.g. silane coupling agents). However, such a means involves other problems such as lowering of storage stability and foaming, and further limited adhesion to some specific substances to be adhered such as stainless steel and aluminum, as well as high cost in the raw material. Thus, such a method is still not suitable for practical use. It is also known that aminoalkoxysilane compounds are excellent for improving adhesion properties of the polyurethane composition when incorporated as an adhesion-promoting agent, but the active hydrogen in the amino group of these compounds is immediately reacted with the active isocyanate group contained in the polyurethane to induce crosslinking reaction, and hence it is very difficult to prepare a composition in the form of a one-pack composition. It is also proposed to use epoxyalkoxysilanes and mercaptoalkoxysilanes as adhesion-promoting agents, but these compounds are not necessarily sufficient for improving the adhesion properties of the composition.

In view of the various drawbacks in the known polyurethane resin composition, the present inventors have intensively studied on an improved polyurethane resin composition having improved adhesion properties. It has now been found that there is useful as an adhesion-promoting agent a reaction product of an alkoxysilyl group-containing amino compound and a carbonyl compound, wherein the primary and/or secondary amine group is converted into a ketimine or enamine group with the carbonyl group and that there can be obtained a polyurethane resin composition having excellent adhesion properties to the substances to be adhered by incorporating the reaction product.

An object of the present invention is to provide an improved polyurethane resin composition having excellent adhesion properties to the substances to be adhered. Another object of the invention is to provide a novel polyurethane resin composition which is incorporated with a reaction product of an alkoxysilyl group-containing amine compound and a carbonyl compound or a mixture thereof. A further object of the invention is to provide an adhesion-promoting agent comprising a reaction product of an alkoxysilyl group-containing amine compound and a carbonyl compound. These and other objects and advantages of the present invention will be apparent to those skilled in the art from the following description.

The polyurethane resin composition of the present invention comprises (A) a urethane prepolymer composition containing 0.5 to 15.0% by weight of an active isocyanate group which is prepared by reacting a polyoxyalkylene ether polyol and/or polyester polyol and an excess amount of a polyisocyanate compound, and (B) 0.05 to 5.0% by weight (based on the whole weight of the composition) of a reaction product of an amine compound containing at least one alkoxysilyl group of the formula:

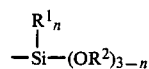

wherein $R^1$ and $R^2$ are the same or different and are each a straight or branched alkyl having 1 to 4 carbon atoms (e.g. methyl, ethyl, propyl, isopropyl, butyl, isobutyl, sec-butyl), and n is 0, 1 or 2, and an excess amount of a carbonyl compound.

The urethane prepolymer composition used in the present invention can be prepared by reacting a polyol such as polyether polyols, polyester polyols, hydroxycontaining polybutadiene polyols, acrylpolyols, castor oil derivatives, tall oil derivatives and an excess amount of a polyisocyanate compound.

The polyether polyols, i.e. polyoxyalkylene ether polyols, are polyoxyethylene-propylene polyols where are a random or block copolymer prepared by ring opening polymerization of propylene oxide and ethylene oxide in the presence of one or more of a low molecular weight active hydrogen compound having two or more active hydrogens and polyoxytetramethylene glycols which are prepared by ring opening polymerization of tetrahydrofuran, and the polyether polyols have two or three hydroxy groups in the molecule. The low molecular weight active hydrogen compounds include diols (e.g. ethylene glycol, propylene glycol, butylene glycol, 1,6-hexanediol), triols (e.g. glycerine, trimethylolpropane, 1,2,6-hexanetriol), and amines (e.g. ammonia, methylamine, ethylamine, propylamine, butylamine). The polyoxyalkylene ether polyols have preferably a molecular weight of 500 to 10,000 and contain two or more three hydroxy groups. There can be used polyols having various molecular weights and various numbers of functional groups depending on the properties required. The polyether polyols may be used alone or in combination of two or more thereof.

Polyester polyols have a terminal hydroxy group and are usually prepared by reaction of a polybasic acid and a polyvalent alcohol or by ring opening polymerization of a polyvalent alcohol and ε-caprolactone. The polybasic acid includes phthalic acid, adipic acid, terephthalic acid, isophthalic acid, sebacic acid, dimeric linoleic acid, maleic acid, and di-lower alkyl esters of these acids. The polyvalent alcohol includes the same diols and triols as mentioned above and further includes diethylene glycol, triethylene glycol, dipropylene glycol, tripropylene glycol, or the like.

When the polyurethane resin composition of the present invention is used as an adhesive or a paint, the polyester polyol and the polyether polyol are preferably used together. Besides, when the polyurethane resin composition of the present invention is used as an adhesive for lamination processing of a synthetic resin film, the polyester polyols may be used alone. Thus, the polyether polyols, polyesther polyols and other polyols may be used alone or in combination of two or more thereof in accordance with the desired properties and utilities.

The polyisocyanate compound to be reacted with the above polyols includes aliphatic polyisocyanates (e.g. hexamethylene diisocyanate, lysine methyl ester diisocyanate), alicyclic polyisocyanates (e.g. hydrogenated diphenylmethane diisocyanate, isophorone diisocyanate, hydrogenated tolylene diisocyanate), aromatic isocyanates (e.g. tolylene diisocyanate (TDI), diphenylmethane diisocyanate (MDI), naphthylene diisocyanate, xylylene diisocyanate), and a mixture of these isocyanates. Particularly preferred isocyanates are aromatic isocyanates, such as TDI and MDI.

The desired urethane prepolymer can be obtained by reacting the above polyols and the above polyisocyanates in such a molar ratio that the active isocyanate group in the polyisocyanates is 1 mole or more to 1 mole of the hydroxy group in the polyols. For instance, both components are reacted in a ratio of $1.3 \leq NCO/OH \leq 10$ at 70° to 100° C. for several hours. The reaction is usually carried out in a solvent in the presence of a catalyst and also using a plasticizer. The urethane prepolymer thus prepared is regulated to the desired range of the active isocyanate content within the range of 0.5 to 15% by weight in accordance with the desired properties and utilities. For example, for the purpose of use as an adhesive and paint, the active isocyanate content is preferably in the range of 3 to 15% by weight, and for the purpose of use as a sealant, the active isocyanate content is preferably in the range of 0.5 to 5.0% by weight.

The amine compound containing at least one alkoxysilyl group includes all known amine compounds and is preferably aminoalkylalkoxysilane compounds of the formula:

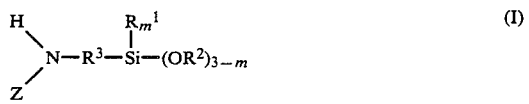
(I)

wherein $R^1$ and $R^2$ are as defined above, $R^3$ is a divalent hydrocarbon group having 1 to 4 carbon atoms (e.g. methylene, ethylene, propylene, butylene), Z is hydrogen atom, or an aminoalkyl having 1 to 4 carbon atoms (e.g. aminomethyl, aminoethyl, aminopropyl, aminobutyl), and m is 0, 1 or 2. Suitable examples of the aminoalkylalkoxysilane compound are N-(β-aminoethyl)aminomethyltrimethoxysilane, γ-aminopropyltriethoxysilane, γ-aminopropylmethyldiethoxysilane, N-(β-aminoethyl)-γ-aminopropyltriethoxysilane, and N-(β-aminoethyl)-γ-aminopropylmethyldimethoxysilane.

Other suitable examples of the amine compound are compounds prepared by reacting with heating under stirring the above-mentioned aminoalkylalkoxysilane compound (I) and less than equimolar amount of an epoxyalkylalkoxysilane compound of the formula:

(II)

wherein $R^1$, $R^2$, $R^3$ and m are as defined above, and G is a glycidoxy or epoxycyclohexyl group. The reaction is preferably carried out by using 1 mole of the aminoalkylalkoxysilane compound (I) and not more than 0.9 mole, preferably 0.1 to 0.6 mole, of the epoxyalkylalkoxysilane compound (II). Suitable examples of the epoxyalkylalkoxysilane compound are γ-glycidoxypropyldimethylethoxysilane, γ-glycidoxypropylmethyldiethoxysilane, γ-glycidoxypropyltrimethoxysilane, β-(3,4-epoxycyclohexyl)ethyltrimethoxysilane, and β-(3,4-epoxycyclohexyl)ethylmethyldimethoxysilane.

These amine compounds have an active hydrogen atom bound to nitrogen atom, and hence, when they are incorporated into the composition as they stand, the active hydrogen reacts immediately with the active isocyanate group contained in the urethane prepolymer to form a urea bond, by which the composition is cured owing to the crosslinking reaction. Accordingly, in the present invention, the amine compound is previously reacted with a carbonyl compound, by which the primary and/or secondary amino group in the amine compound is subjected to dehydration condensation reaction with the carbonyl group to form an enamine group or ketimine group (i.e. the amino group being blocked), and the amine compound is incorporated in the form of a blocked state into the composition in the absence of moisture. Since the blocked compound is easily converted into the original amine compound and carbonyl compound by hydrolysis when contacted with moisture in air, the composition should be kept in the state of being sufficiently sealed from moisture.

The carbonyl compound includes all known compounds, and includes, for example, aldehydes (e.g. acetaldehyde, propionaldehyde, n-butyraldehyde, isobutyraldehyde, diethylacetaldehyde, glyoxal, benzaldehyde), cyclic ketones (e.g. cyclopentanone, trimethylcyclopentanone, cyclohexanone, trimethylcyclohexanone), aliphatic ketones (e.g. acetone, methyl ethyl ketone, methyl propyl ketone, methyl isopropyl ketone, methyl isobutyl ketone, diethyl ketone, dipropyl ketone, diisopropyl ketone, dibutyl ketone, diisobutyl ketone), and β-dicarbonyl compounds of the formula:

$$R^4-CO-CH_2-CO-R^5$$
(III)

wherein $R^4$ and $R^5$ are the same or different and are each an alkyl having 1 to 16 carbon atoms (e.g. methyl, ethyl, propyl, butyl, hexyl, heptyl, octyl, nonyl, decyl, undecyl, hexadecyl, etc.), an aryl having 6 to 12 carbon atoms (e.g. phenyl, tolyl, xylyl, naphthyl, etc.), or an alkoxy having 1 to 4 carbon atoms (e.g. methoxy, ethoxy, propoxy, butoxy, etc.), such as acetylacetone, methyl acetoacetate, ethyl acetoacetate, dimethyl malonate, diethyl malonate, methyl ethyl malonate, dibenzoylmethane, or the like. Among these carbonyl compounds, the preferred one is the β-dicarbonyl compounds (III) which contain an active methylene group.

The reaction of the above amine compound and carbonyl compound is usually carried out under conditions similar to those of the dehydration condensation reaction between an aldehyde and a ketone, for instance, in the presence of a dehydrating agent or while distilling off water under reflux. More specifically, the reaction is carried out by mixing an amine compound and a stoichiometrically equivalent or excess amount of a carbonyl compound (in case of the β-dicarbonyl compound (III), one of the two keto groups being reacted) in a suitable organic solvent (e.g. toluene, xylene, benzene), adding thereto a dehydrating agent (e.g. anhydrous magnesium sulfate), and reacting the mixture with stirring at room temperature or at an elevated temperature.

The amino-blocked reaction product of the amine compound and the carbonyl compound obtained above can be used alone or in combinations of two or more thereof.

The amino-blocked reaction product thus obtained or a mixture thereof is incorporated into the urethane prepolymer composition in an amount of 0.05 to 5.0% by weight based on the whole weight of the composition to give the desired polyurethane resin composition having excellent properties. When the reaction product is used in an amount of less than 0.05% by weight, the resulting composition can not show the desired improved adhesion properties, but on the other hand, when the amount of the reaction product is over 5.0% by weight, curing of the polyurethane composition is undesirably occasionally inhibited because the silyl group is hydrolised to form an alcohol which reacts with the isocyanate.

The polyurethane resin composition of the present invention may optionally be incorporated with other various additives such as fillers, plasticizers, solvents, catalysts, antioxidants, pigments or the like.

Inert fillers usable in the present invention include carbon black, calcium carbonate, clay, talc, etc. which may be used alone or in combinations of two or more thereof. The filler may be used in an amount of 20 to 70% by weight. Plasticizers include phthalates (e.g. dioctyl phthalate, butyl benzyl phthalate, dinonyl phthalate, etc.), benzoates (e.g. diethylene glycol dibenzoate, ethylene glycol monobutyl ether benzoate, etc.), partially hydrogenated terphenyls, alkyl-polycyclic aromatic hydrocarbons, chlorinated paraffins, which may be used in an amount of not more than 20% by weight. Solvents include aromatic hydrocarbons (e.g. toluene, xylene, etc.), esters (e.g. ethyl acetate, etc.), ketones (e.g. acetone, methyl ethyl ketone, etc.), ethers (e.g. diethyl ether, methyl ethyl ether, etc.). These fillers, plasticizers and solvents should be inert to the polyurethane resins and also should be anhydrous, and hence, they are used after drying or dehydration.

The catalyts used for promoting the curing of the composition include N-alkylbenzylamines, N-alkylmorpholines, N-alkyl aliphatic polyamines, N-alkylpiperazines, triethylenediamine, naphthenate or octanoate of a heavy metal (e.g. tin, lead, cobalt, manganese or iron), dibutyl tin dilaurate, dibutyl tin maleate, or the like.

The polyurethane resin composition of the present invention may also optionally be incorporated with silicic anhydrate, antioxidants, ultraviolet adsorbers, thickening agents.

The polyurethane resin composition of the present invention may be in the form of a two-pack composition, but is preferably in the form of a one-pack composition in view of easy handling and good appearance because even though both components are incorporated, the composition can stably be kept for a long period of time without undesirable increase of viscosity and gelation. The composition can be prepared in a conventional manner, for example, by reacting with heating a polyol compound and a polyisocyanate compound to form a urethane prepolymer in a closed stirring kneader provided with a jacket for keeping the temperature, and adding thereto dried fillers, pigments, plasticizers, solvents and other additives in order, and adding finally a reaction product of an amine compound and a carbonyl compound or a mixture thereof, and then kneading with stirring the mixture to give the desired composition.

The polyurethane resin composition of the present invention is useful as an adhesive, sealant, primer, paint, coating agent and for any other utilities for which conventional polyurethane resin compositions are used.

The kinds and amounts of the components to be incorporated in the polyurethane resin composition of the present invention may vary in accordance with the utilities of the composition. For example, when it is used as an adhesive, paint or primer, the composition is preferably tough, and hence, the urethane prepolymer composition has preferably a content of an active isocyanate group of 7 to 15% by weight. Besides, when it is used as a sealant or coating agent, the urethane prepolymer has preferably a content of an active isocyanate group of 0.5 to 5.0% by weight in order to give rubbery elasticity having a high degree of elongation and to prevent undesirable foam due to carbon dioxide which is produced by the reaction with moisture during the curing treatment. Moreover, when it is used as a paint, primer or coating agent which requires color fastness, the starting polyisocyanate for the urethane prepolymer is preferably aliphatic polyisocyanates, and when it is used as an adhesive or paint suitable for adhering or coating plastic substances (e.g. polyvinyl chloride substance), the other starting polyols for the urethane prepolymer is preferably a polyester polyol alone or a combination thereof with a polyether polyol.

The composition of the present invention can also show excellent adhesiveness to metals, particularly stainless steel, aluminum plates, zinc-treated steel panels which are hardly adhered with the conventional compositions, and further can improve the properties of the substances treated with the compositions of the present invention, because when the composition of the present invention is applied to, the amino-blocked amine compound is deblocked with water and then the amine compound is reacted with the isocyanate to produce crosslinking.

The present invention is illustrated by the following Examples, but should not be construed to be limited thereto. In Examples, "part" and "%" mean part by weight and % by weight, respectively, unless specified otherwise.

EXAMPLE 1

(a) Preparation of urethane prepolymer

Polyoxyalkylene ether diol (molecular weight: 2,600, Sunnix PL-2100 ®, manufactured by Sanyo Kasei K.K.) (50 parts), polyester polyol (polypropylene glycol adipate, Adeca New Ace ®F7-67, manufactured by Asahi Denka Kogyo K.K.) (50 parts) and diphenylmethane 4,4'-diisocyanate (100 parts) are charged into a reactor provided with a jacket for keeping elevated temperature which is purged with nitrogen gas. The mixture is reacted with stirring at 80° C. for 4 hours to give a polyurethane prepolymer (active isocyanate content: 14%, viscosity: 10,000 cps).

(b) Preparation of amino-blocked amine compound

Into a reactor purged with nitrogen gas are charged dry toluene (150 parts), N-(β-aminoethyl)-γ-aminopropyltrimethoxysilane (22.2 parts) and molecular sieves (15 parts, as a dehydrating agent), and thereto is further added dropwise with stirring acetylacetone (20 parts). After the addition, the mixture is reacted with stirring at room temperature for 4 hours. After the reaction, the dehydrating agent is removed by filtration with suction to give a solution of an amino-blocked amine compound in toluene. This solution has a content of the active ingredient of 22%.

(c) Preparation of polyurethane resin composition

To the urethane prepolymer obtained in the above (a) (50 parts) are added dried calcium carbonate (water content: less than 0.5%) (30 parts), clay (10 parts), the solution of an amine compound obtained in the above (b) (1.0 part) and xylene (5 parts), and the mixture is stirred to give a polyurethane resin composition. The composition thus obtained has a viscosity of 10,000 cps and an active isocyanate content of 7.3%, and shows excellent storage stability, i.e. even after having been kept at 50° C. for one month in sealed state, the viscosity is still 12,000 cps.

(d) Use of the composition as a one-pack, wet-curable adhesive

The urethane resin composition obtained in the above (c) was evenly applied to a plywood (width: 25 mm, length: 100 ml, thickness: 3 mm) in a thin layer (applied amount: 160 g/m²), and the plywood was laminated with a stainless steel panel (the same width and length as the plywood, thickness: 0.2 mm). The laminated product was kept in a room having a constant temperature and a constant humidity of 20° C./65% RH for 48 hours in order to subject to aging and curing.

The cured product thus obtained had a 180° peeling strength (the initial adhesion strength) of 3.0 kg/25 mm. Besides, this cured product was immersed in water at 40° C. for one month, and then the adhesion strength was measured. As a result, it showed a water resistant adhesion strength of 4.0 kg/25 mm.

In the same manner as described above except that a polyvinyl chloride-made decorative sheet was used instead of the stainless steel panel, the above test was repeated. As the result, it showed an initial adhesion strength of 5.0 kg/25 mm and a water resistant adhesion strength of 4.0 kg/25 mm.

REFERENCE EXAMPLE 1

In the same manner as described in Example 1, (c) except that no amino-blocked amine compound is used, a polyurethane resin composition is prepared.

By using this urethane resin composition, the tests of adhesion strength to stainless steel panel were repeated in the same manner as described in Example 1, (d). As a result, it showed an initial adhesion strength of 1.0 kg/25 mm, in which interface of the stainless steel panel and the adhesive was broken, and showed a water resistant adhesion strength of 0.2 kg/25 mm. Thus, the adhesion strength was significantly decreased after immersing in water.

EXAMPLE 2

(a) Preparation of urethane prepolymer

In the same manner as described in Example 1, (a), a polyoxyalkylene ether triol (molecular weight: 7,000, Sunnix ®FA 907, manufactured by Sanyo Kasei Kogyo K.K.) (744 parts) and tolylene diisocyanate (TDI) (56 parts) are reacted to give a urethane prepolymer (isocyanate content: 1.8%, viscosity: 50,000 cps).

(b) Preparation of amino-blocked amine compound

γ-Aminopropyltriethoxysilane (22.1 parts) and γ-glycidoxypropyltrimethoxysilane (7.03 parts) (molar ratio: 1:03) are added to dry toluene (150 parts), and the mixture is reacted with stirring at 50° C. for several hours to give a mixture containing aminoalkoxysilanes having an unreacted amino group and imino group.

To a solution of the above mixture (179.13 parts) in toluene is added molecular sieves (15 parts), and thereto is further added dropwise with stirring ethyl acetoacetate (26 parts) at room temperature, and the mixture is reacted with stirring at room temperature for 6 hours to give an amino-blocked amine compound.

(c) Preparation of polyurethane resin composition

Into a sealed tank are charged the urethane prepolymer obtained in the above (a) (30 parts), dioctyl phthalate (15 parts), a previously heat-dried titanium oxide (10 parts), calcium carbonate (40 parts) and silicic acid anhydride (3 parts), and the mixture is stirred under reduced pressure for 60 minutes. To the mixture are added the amino-blocked amine compound obtained in the above (b) (1.5 part) and dibutyl tin dilaurate (0.5 part, as a catalyst) to give a polyurethane resin composition in the form of a highly viscous paste (viscosity: 300,000 cps). This composition is not solidified even after being kept at 50° C. for 14 days in the sealed state and shows excellent storage stability.

(d) Use of the composition as a one-pack, wet-curable sealant

The polyurethane resin composition obtained in the above (c) was applied to an aluminum plate (width: 50 mm, length: 50 mm, thickness 5 mm) in a shape of bead (width: 10 mm), and the applied plate was subjected to aging and curing under the atmosphere of 35° C./90% RH for 3 days. After the curing, one end of the cured sealant was pulled to evaluate the adhesion properties. As a result, it showed cohesion break and showed excellent adhesion properties without necessity of use of a primer. Besides, in the test of water resistant adhesion strength after having been immersed in water at 40° C. for one month in the same manner as described in Example 1, (d), it showed cohesion failure of the sealant, likewise.

REFERENCE EXAMPLE 2

In the same manner as described in Example 2, (c) except that no amino-blocked amine compound is used, a polyurethane resin composition is prepared.

By using this urethane resin composition, the test of tension was repeated in the same manner as described in Example 2, (d). As a result, it showed an interface failure between the aluminum plate and the sealant. When a primer (Primer UM-2, manufactured by Sunstar Giken K.K.) was applied to before application of the polyurethane resin composition, the sealant showed a cohesion failure.

EXAMPLES 3 TO 9

In the same manner as described in Example 1, (b), various amino-blocked amine compounds are prepared by using various components as shown in Table 1.

TABLE 1

| Components | Example No. | | | | | | |
|---|---|---|---|---|---|---|---|
| | 3 | 4 | 5 | 6 | 7 | 8 | 9 |
| Amine compounds: | | | | | | | |
| N—(β-Aminoethyl)-γ-aminopropyl-methyldimethoxysilane | — | — | — | 20.6 | 20.6 | — | — |
| N—(β-Aminoethyl)-γ-aminopropyl-trimethoxysilane | — | 22.2 | 22.2 | — | — | 22.2 | 22.2 |
| γ-Aminopropyltriethoxysilane | 22.1 | — | — | — | — | — | — |
| γ-Glycidoxypropyltrimethoxysilane | — | 7.03 | 4.7 | — | 11.7 | 16.4 | 16.4 |
| Carbonyl compounds: | | | | | | | |
| Acetylacetone | 20 | — | — | — | 20 | — | — |
| Ethyl acetoacetate | — | 26 | — | — | — | 26 | — |
| Diethyl malonate | — | — | 32 | — | — | — | — |
| Cyclohexanone | — | — | — | 9.8 | — | — | — |
| Methyl ethyl ketone | — | — | — | — | — | — | 72 |

By using various amino-blocked amine compounds as obtained above, various polyurethane resin compositions are prepared in the same manner as described in Example 1, (c).

The polyurethane resin compositions were subjected to the tests for initial adhesion strength and water resistant adhesion strength in the same manner as described in Example 1, (d). The results are shown in Table 2.

Besides, by keeping the polyurethane resin compositions at 40° C., and the days until the composition were solidified were counted in order to evaluate the storage stability. The results are also shown in Table 2.

The polyurethane resin compositions were also excellent in heat resistance and water resistance.

TABLE 2

| Properties | Example No. | | | | | | |
|---|---|---|---|---|---|---|---|
| | 3 | 4 | 5 | 6 | 7 | 8 | 9 |
| Initial adhesion strength (kg/25 mm) | 6.5 | 6.5 | 6.5 | 7.0 | 7.0 | 7.5 | 6.5 |
| Water resistant adhesion strength (kg/25 mm) | 4.1 | 5.5 | 5.3 | 3.0 | 5.5 | 5.0 | 3.0 |
| Storage stability (keeping at 40° C.) | More than 21 days | More than 21 days | More than 21 days | 7 days | More than 21 days | More than 21 days | 3 days |

What is claimed is:

1. A polyurethane resin composition comprising
   (A) a urethane prepolymer composition containing 0.5 to 15.0% by weight based on said prepolymer composition of an active isocyanate group, said prepolymer composition prepared by reacting (1) a polyoxyalkylene ether polyol and/or polyester polyol and (2) a stoichiometric excess of a polyisocyanate compound and
   (B) 0.05 to 5.0% by weight based on the polyurethane resin composition of a reaction product of (1) an amine compound having a primary and/or secondary amino group and containing at least one alkoxysilyl group of the formula:

$$-\underset{|}{\overset{R^1_n}{Si}}-(OR^2)_{3-n}$$

wherein $R^1$ and $R^2$ are the same or different and are each alkyl having 1 to 4 carbon atoms and n is 0, 1 or 2, and (2) a stoichiometrically equivalent or excess amount of a carbonyl compound selected from the group consisting of an aldehyde, a cyclic ketone, an aliphatic ketone, and a β-dicarbonyl compound of the formula:

$$R^4-CO-CH_2-CO-R^5$$

wherein $R^4$ and $R^5$ are the same or different and each are an alkyl having 1 to 16 carbon atoms, an aryl having 6 to 12 carbon atoms, or an alkoxy having 1 to 4 carbon atoms, said reaction product containing enamine or ketimine groups formed by a dehydration condensation reaction of the carbonyl group of said carbonyl compound with the primary and/or secondary amino group of said amine compound.

2. The composition according to claim 1, wherein the amine compound containing an alkoxysilyl group is a compound of the formula:

$$\underset{Z}{\overset{H}{\diagdown}}N-R^3-\underset{|}{\overset{R^1_m}{Si}}-(OR^2)_{3-m} \qquad (I)$$

wherein $R^1$ and $R^2$ are the same or different and are each a alkyl having 1 to 4 carbon atoms, $R^3$ is a divalent hydrocarbon group having 1 to 4 carbon atoms, Z is hydrogen atom, or an aminoalkyl having 1 to 4 carbon atoms, and m is 0, 1 or 2.

3. The composition according to claim 1, wherein the amine compound containing an alkoxysilyl group is a compound prepared by reacting an aminoalkylalkoxysilane of the formula:

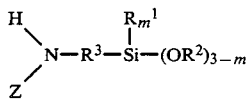  (I)

wherein $R^1$ and $R^2$ are the same or different and are each a alkyl having 1 to 4 carbon atoms, $R^3$ is a divalent hydrocarbon group having 1 to 4 carbon atoms, Z is hydrogen atom, or an aminoalkyl having 1 to 4 carbon atoms, and m is 0, 1 or 2, and less than equimolar amount of an epoxyalkylalkoxysilane compound of the formula:

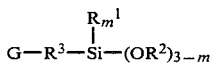  (II)

wherein $R^1$, $R^2$, $R^3$ and m are as defined above, and G is a glycidoxy or epoxycyclohexyl group.

4. The composition according to claim 1, wherein the carbonyl compound is a β-dicarbonyl compound of the formula:

$$R^4-CO-CH_2-CO-R^5 \qquad (III)$$

wherein $R^4$ and $R^5$ are the same or different and are each an alkyl having 1 to 16 carbon atoms, an aryl having 6 to 12 carbon atoms, or an alkoxy having 1 to 4 carbon atoms.

* * * * *